United States Patent [19]

Gray

[11] Patent Number: 5,437,279

[45] Date of Patent: Aug. 1, 1995

[54] METHOD OF PREDICTING CARCINOMIC METASTASES

[75] Inventor: Lincoln C. Gray, Houston, Tex.

[73] Assignee: Board of Regents, The University of Texas System, Austin, Tex.

[21] Appl. No.: 908,239

[22] Filed: Jul. 2, 1992

[51] Int. Cl.$^6$ .......................... A61B 6/03; A61B 5/00
[52] U.S. Cl. .............................. 128/653.1; 128/653.2; 128/898
[58] Field of Search ................... 128/653.1, 898, 653.2; 364/413.02, 413.13, 413.14, 413.17, 413.22, 413.1

[56] References Cited

U.S. PATENT DOCUMENTS

| | | | |
|---|---|---|---|
| 4,907,156 | 3/1990 | Doi et al. | 364/413.13 |
| 5,023,785 | 6/1991 | Adrion et al. | 364/413.08 |
| 5,101,827 | 4/1992 | Goldenberg | 128/653.4 |
| 5,115,816 | 5/1992 | Lee | 128/749 |

FOREIGN PATENT DOCUMENTS 0822200  4/1981  U.S.S.R. .......................... 364/413.02

OTHER PUBLICATIONS

Gray et al., "Multidimensional Scaling of Head and Neck Metastasts", Int. J. Biomed. Comp., 31 (1992), pp. 177-187.

Batsakis J. G., Medina J. E., "Pathological evaluation of neck dissection lymph nodes: A status report", Cancer in the Neck: Evaluation and Treatment (Eds: D. L. Larson, A. J. Ballentyne and O. M. Guillamondegui) McMillan, NY, 1986, pp. 33-40.

Lindberg R, "Distribution of cervical lynph node metastases form squamous cell carcinoma of the upper respiratory and digestive tracts", Cancer, 29 (1972) 1446-1449.

Meissner W. A., "Pathological evaluation and classification of tumors", Cancer: A Manual for Practitioners, American Cancer Society, Boston, 1978.

J. Douglas Carroll & Jih-Jie Chang, "Analysis of Individual Differences in Multidimensional Scaling Via an N-Way Generalization of 'Eckart-Young' Decomposition", Psychometrika, 1970, pp. 283-319.

Joseph B. Kruskal & Myron Wish, "Multidimensional Scaling", Sage University Paper series on Quantitative Applications in the Social Sciences, Series No. 07/011, 1978, Beverly Hills and London: Sage Publications.

Susan S. Schiffman, M. Lance Reynolds & Forrest W. Young, "Introduction to Multidimensional Scaling-Theory, Methods, and Applications", Academic Press, Inc., 1981, pp. 55-85, 143-168.

*Primary Examiner*—Krista M. Zele
*Attorney, Agent, or Firm*—Arnold, White & Durkee

[57] ABSTRACT

A method of predicting the locations of the lymph nodes most at risk of metastasis from a primary tumor of, e.g., the neck or head. The method utilizes data on the location of the primary tumor and the identity of lymph nodes to which the cancer has already spread. The data are transformed by a weighted multidimensional scaling (WMDS) process; points representing clusters of lymph nodes are placed in an imaginary mathematical space such that distances between points in that space are proportional to differences in the occurrence frequency of metastases.

1 Claim, 7 Drawing Sheets

DATA RELATED TO NODAL CLUSTERS
OLD RAW DATA

| IPSILATERAL NODAL CLUSTERS | O | F | R | S | T | B | P | L | H |
|---|---|---|---|---|---|---|---|---|---|
| 1 SUBMENTAL | 5 | 5 | 1 | 1 | 1 | 2 | 2 | 1 | 1 |
| 2 SUBMAXILLARY | 34 | 50 | 26 | 2 | 16 | 10 | 5 | 2 | 2 |
| 3 UPPER JUGULAR | 89 | 43 | 94 | 30 | 103 | 127 | 78 | 98 | 148 |
| 4 MIDDLE JUGULAR | 16 | 11 | 25 | 9 | 25 | 57 | 31 | 70 | 112 |
| 5 LOWER JUGULAR | 4 | 5 | 5 | 2 | 14 | 13 | 7 | 22 | 43 |
| 6 UPPER POSTERIOR CERVICAL | 0 | 1 | 3 | 0 | 10 | 8 | 9 | 5 | 8 |
| 7 MIDDLE POSTERIOR CERVICAL | 0 | 0 | 1 | 0 | 6 | 8 | 7 | 2 | 9 |
| 8 LOWER POSTERIOR CERVICAL | 1 | 1 | 0 | 0 | 8 | 2 | 4 | 6 | 14 |
| 9 SUPRACLAVICULAR | 0 | 1 | 0 | 0 | 0 | 6 | 3 | 5 | 6 |
| CONTRALATERAL NODAL CLUSTERS | | | | | | | | | |
| (1) SUBMENTAL | 2 | 0 | 0 | 1 | 0 | 1 | 0 | 0 | 0 |
| (2) SUBMAXILLARY | 4 | 4 | 0 | 1 | 3 | 0 | 0 | 0 | 0 |
| (3) UPPER JUGULAR | 9 | 5 | 9 | 10 | 14 | 45 | 21 | 31 | 18 |
| (4) MIDDLE JUGULAR | 4 | 0 | 4 | 2 | 3 | 10 | 5 | 14 | 7 |
| (5) LOWER JUGULAR | 1 | 1 | 1 | 0 | 2 | 4 | 3 | 8 | 4 |
| (6) UPPER POSTERIOR CERVICAL | 0 | 0 | 0 | 0 | 2 | 0 | 2 | 0 | 2 |
| (7) MIDDLE POSTERIOR CERVICAL | 0 | 0 | 0 | 1 | 3 | 2 | 3 | 3 | 2 |
| (8) LOWER POSTERIOR CERVICAL | 0 | 0 | 0 | 0 | 2 | 1 | 1 | 3 | 0 |
| (9) SUPRACLAVICULAR | 0 | 0 | 0 | 0 | 0 | 1 | 2 | 2 | 1 |
| TOTAL | 169 | 127 | 169 | 59 | 212 | 297 | 183 | 272 | 377 |

DATA RELATED TO NODAL CLUSTERS
NEW RAW DATA

| O | F | R | S | T | B | P | L | H | NODALGRAM X | Y |
|---|---|---|---|---|---|---|---|---|---|---|
| 4 | 8 | 1 | 0 | 0 | 0 | 1 | 2 | 3 | -.137 | .116 |
| 37 | 30 | 20 | 3 | 7 | 10 | 6 | 20 | 39 | -.113 | .072 |
| 40 | 20 | 18 | 4 | 8 | 23 | 10 | 34 | 62 | .106 | .017 |
| 23 | 15 | 9 | 2 | 3 | 9 | 4 | 31 | 56 | -.056 | .109 |
| 11 | 5 | 3 | 0 | 2 | 4 | 2 | 10 | 23 | -.110 | .114 |
| 5 | 2 | 1 | 0 | 0 | 1 | 0 | 3 | 9 | -.117 | .115 |
| 6 | 0 | 4 | 0 | 0 | 0 | 1 | 1 | 8 | -.124 | .125 |
| 4 | 1 | 2 | 0 | 0 | 1 | 0 | 0 | 5 | -.133 | .127 |
| 1 | 0 | 0 | 0 | 0 | 1 | 0 | 0 | 1 | -.135 | .127 |
| 1 | 1 | 0 | 0 | 0 | 0 | 0 | 0 | 0 | -.122 | .050 |
| 1 | 7 | 0 | 0 | 0 | 2 | 1 | 7 | 0 | .129 | -.528 |
| 4 | 6 | 1 | 1 | 1 | 5 | 3 | 16 | 15 | .816 | -.742 |
| 2 | 2 | 0 | 0 | 0 | 2 | 1 | 11 | 4 | .371 | -.140 |
| 1 | 1 | 1 | 0 | 0 | 1 | 0 | 2 | 3 | .029 | .028 |
| 0 | 1 | 0 | 1 | 0 | 0 | 0 | 3 | 0 | -.088 | .092 |
| 0 | 0 | 0 | 0 | 0 | 0 | 0 | 2 | 0 | -.092 | .093 |
| 0 | 0 | 0 | 0 | 0 | 0 | 0 | 1 | 0 | -.104 | .100 |
| 0 | 0 | 0 | 0 | 0 | 0 | 0 | 0 | 0 | -.119 | .125 |
| 140 | 99 | 60 | 22 | 32 | 59 | 29 | 143 | 228 | 0 | 0 |

DATA RELATED TO PRIMARY TUMORS

| SYMBOL | NAME | PRIMARY WEIGHTS* | | BEST CENTER | | CORRELATIONS | |
|---|---|---|---|---|---|---|---|
| | | X | Y | X | Y | WMDS | FINAL |
| O | ORAL TONGUE | .262 | .776 | .80 | -1.00 | .992 | .995 |
| F | FLOOR OF MOUTH | -.391 | 1.209 | -1.00 | -.74 | .942 | .997 |
| R | RETROMOLAR TRIGONE | .296 | .741 | .80 | -1.00 | .987 | .993 |
| S | SOFT PALATE | .740 | .268 | .82 | -.75 | .961 | .982 |
| T | TONSIL | .447 | .594 | .92 | -1.00 | .980 | .992 |
| B | BASE OF TONGUE | .967 | .025 | .99 | -.73 | .986 | .992 |
| P | PHARYNGEAL WALL | .855 | .159 | .82 | -.74 | .983 | .993 |
| L | SUPRAGLOTTIC LARYNX | 1.174 | -.300 | .90 | .99 | .962 | .993 |
| H | HYPOPHARYNX | 1.078 | -.194 | .98 | .44 | .937 | .979 |

FIG. 8

METHOD OF PREDICTING CARCINOMIC METASTASES

BACKGROUND OF THE INVENTION

Squamous cell carcinomas are the most common cancer in the mucous membranes of the nose and throat. These account for about 3% of the cancers in the United States, resulting in about 30,5000 new cases per year.

The initial tumor is called the "primary." Primaries occur in various regions of the upper aerodigestive tract such as the tongue, tonsil, palate, etc.

Primary tumors have a tendency to spread (metastasize) to nearby lymph nodes. The lymph nodes trap the spreading tumor cells, but then the tumor starts to grow in these nodes and can then spread further. Lymph nodes of the head and neck occur in "clusters" named to indicate where the cluster is found, such as submental (below the chin), upper jugular (high in the anterior part of the neck), lower posterior cervical (low in the back of the neck), and so forth. Nodal clusters are similar on both sides of neck.

Lymph node clusters that contain tumor cells are called "positive." In relatively advanced cases, positive clusters can be detected by feeling a lump in the neck. These are termed clinical metastases because they are detected without pathologic confirmation. A problem with clinical data is that small positive nodes can be missed. Positive clusters can also be detected by a pathologist, who microscopically examines the nodes as they are removed during surgery.

A problem with pathological data about lymph nodes is that a node normally must be removed before it is known whether or not it is diseased. Further surgical treatment usually requires excision of both the primary tumor and any nodal clusters which have a high risk for metastases. Post-operative radiotherapy is sometimes used to kill any remaining malignant cells. The surgery, termed a neck dissection, may be of the radical type where all of the nodal clusters are removed, or of the selective type where only clusters thought to be positive are removed.

It is plainly desirable to detect and to remove all the positive nodes in order to prevent recurring tumors. It is likewise desirable to removed no more nodes than necessary in order to minimize the patient's post-operative morbidity. Any knowledge of consistent patterns in cervical metastases would thus be of value.

Unfortunately, although certain patterns in the spread of these tumors are recognized, these patterns are complicated. Tumors do not simply spread to the next physically nearest nodes. Nodes in close physical proximity to the primary may actually be less likely to be positive than more distant nodes. This can occur due to normal anatomic pathways which bypass adjacent nodal clusters. Complex patterns can also arise because the presence of tumor or previous treatment may cause aberrant pathways of lymphatic drainage by blocking normal channels.

The complexity is further increased because different primaries have different patterns of spread, even though the same nodal clusters are involved. For example, metastases can occur to both sides of the neck in some but not all cases as the primary approaches the midline.

Studies have been done which indicate the absolute frequency of occurrence of metastases for the various clusters of lymph nodes from each possible primary. These data are usually reported in multiple tables of positive nodes from different primaries. This traditional presentation is not in a form where complex patterns are readily apparent, however, head and neck surgeons, until now, have been forced to rely on their own experience when trying to determine which clusters the primary has metastasized during surgical excision of infected lymph nodes or during postoperative consultation with the patient.

SUMMARY OF THE INVENTION

An illustrative method in accordance with the invention predicts the locations of the lymph nodes most at risk of metastasis from a primary tumor associated with a cancer of the neck or head. In order to make predictions, the method requires input data on the location of the primary tumor and the identity of lymph nodes to which the cancer has already spread.

Using clinical studies conducted on the spread of head and neck tumors, the method makes use of a data transformation by a process known as weighted multidimensional scaling (WMDS), which successfully quantifies a pattern in the spread of these tumors. WMDS places points (representing clusters of lymph nodes) in an imaginary mathematical space such that distances between points in that space are proportional to differences in the occurrence frequency of metastases. WMDS also generates a set of weight values, with each weight corresponding to a different primary site. These weights are significant, since their components express the scaling factor applicable to each dimension of the imaginary nodal space to determine a space of nodal values unique to each specific primary site. It is noted that this analytical approach explains vastly more of the input data than expected by chance, and essentially the same result has been obtained from two different sets of study data.

Using this process, the data transformation underlying the illustrative method allows the display of the results of this analysis in such a way that the important predictions about patterns in the spread of head and neck cancers are easily visualized. Spreading cancer is modeled as an expanding ellipse in the imaginary space, termed "nodalgram space." Several parameters are estimated in order to do this including the center of the ellipse and the ratio of the ellipse's axis. Once the position and shape of the ellipse are estimated, the order in which nodes are encountered in the imaginary space as the ellipse expands is determined. The relative probabilities of metastases may then be depicted as, e.g., changing colors on a realistic image of the human head.

The illustrative method therefore allows a user to input, for a given patient, data concerning the location of the primary and any clusters of lymph nodes which are known to be infected. For a given primary, the method determines the center of the ellipse by table lookup from a set of iteratively-computed best correlations between a particular primary site, the nodalgram, and the raw data. From this determined value, the cancer is "grown" temporally by a use of the model which may be thought of as an expanding ellipse, the major and minor axis ratio of which is obtained from the previously-calculated MDS weights of the primary site input by the user. The relative probability that each cluster of lymph nodes in the patient's neck will be infected as a function of time is given by the order in which that cluster is reached as the ellipse is expanded. These probabilities are displayed as indices and are sued by the treating physician to identify those nodes which are most at risk of contracting cancer. The treating physician may also use the technique of the present invention during excision of infected nodes to predict which nodes should be removed based on the known location of the primary tumor and the condition of previously-removed nodes. These data are input into a computer, which may refine its predictions based on the most current data to generate accurate predictions of which nodes are the most likely to be infected and therefore most in need of removal.

Another use of the illustrative method of the present invention relates to locating an unknown primary when the treating physician has identified one or more infected lymph nodes. In this application, the data concerning the location of the infected nodes are input into the computer model, which identifies likely primary sites by computing an ellipse which includes the infected sites and "shrinking" the ellipse to determine its center, which corresponds to the tumor site in the imaginary space. Using the reverse of the original process, this point may be transformed back into anatomical coordinates and located on the patient.

BRIEF DESCRIPTION OF THE DRAWINGS

FIGS. 7 and 8 are data tables discussed in more detail below.

DETAILED DESCRIPTION OF SPECIFIC EMBODIMENTS

Figure 1:
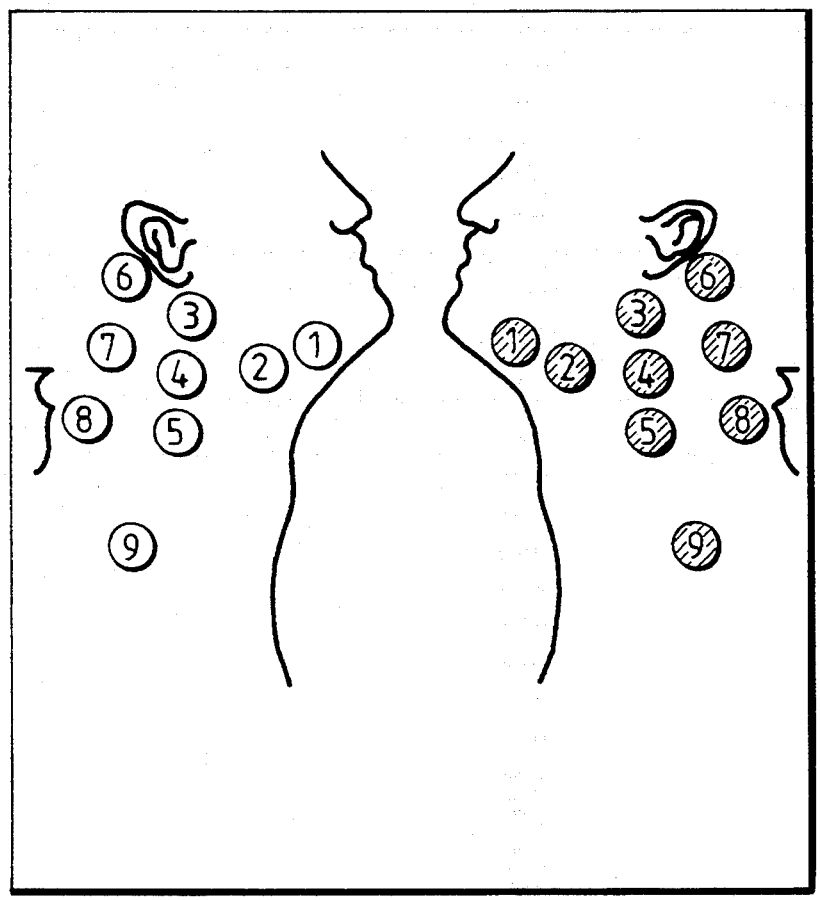
FIG. 1 is a side view depicting the location of the major clusters of lymph nodes in the neck region.

Understanding of the present invention is aided by a brief review of the mathematical concept of multidimensional scaling (MDS), which is used here to transform data from past studies into a form which is usable by the illustrative method in making predictions. One useful reference in this subject area is Schiffman, Introduction to Multidimensional Scaling: Theory, Methods, and Applications Orlando: Academic Press (1981).

In the present analysis, two nodal clusters that are likely to either both the positive or both be negative are considered to be similar, and hence "close together" in an abstract sense. Pairs of nodal clusters where one is positive and one is negative are considered dissimilar and hence "far apart" (even though they may be physically adjacent). Thus, proximities between clusters can be measured in a non-traditional or abstract way, such as similarities in the chance of trapping metastases, as well as in traditional distances.

A set of proximities can be used to calculate coordinates of points which can then be plotted to form a "map," such that distances in the map match the input measures as closely as possible. In this analysis the nodal clusters are positioned in an imaginary space, termed nodalgram space, to match the data on occurrence of metastases.

It is easier to think of this process in the reverse, that is creating a matrix of proximities from a map of points. A simple example of this reverse process is the table of mileage between all possible pairs of cities at the bottom of a highway map. Multidimensional scaling does the reverse, creating a map from distances. Specifically, given a set of proximities measured between all possible pairs of nodal clusters, MDS calculates coordinates of points representing these clusters (in any specified number of dimensions), maximizing the correlation between the input measures and distances between the points.

The variance accounted for (VAF) by the MDS analysis, defined as the squared correlation between the normalized proximities and corresponding distances on the map, determines if a consistent pattern exits. The map produced by MDS is a succinct visual as well as mathematical representation of that pattern. Thus, MDS has two uses: To detect and to display a pattern.

Often, proximities can be derived from more than one source, and then differences between those sources can be used to glean more information about the underlying pattern. This is applicable to the illustrative method because patterns of metastasis have been recorded for each of several different primaries. The extent to which a single underlying pattern can be transformed to match the proximities from each different source is calculated. This technique, called weighted multidimensional scaling (WMDS), utilizes a matrix of proximities from each source and separately displays information that is common to all of the data and weights that are unique to each source.

Proximity measures are derived for all possible pairs of nodal clusters for each of several primaries. Weighted multidimensional scaling is used to create a "nodalgram", a map of these clusters arranged in an imaginary space, such that the distances between clusters are maximally correlated with the extent of disease. WMDS also creates a second plot (here termed the "primary weights") showing the extent to which the tumors from each primary spread along the dimensions of the nodalgram.

Figure 2:
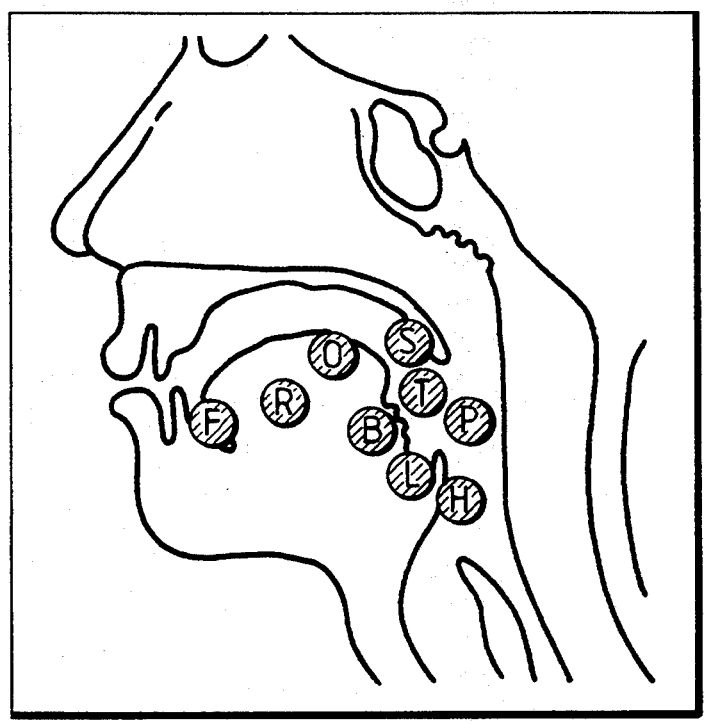
FIG. 2 is a side view depicting the most common sites for primary tumors in the neck region.

MDS was applied to two large sets of data on cervical metastasis. The data were collected in different ways and over different decades. Lindberg published distributions of positive nodal clusters in 1155 patients with previously untreated squamous cell carcinoma of the head and neck, in Cancer, 29 (1972) at 1446-49. Numbers of clinically positive clusters were recorded for 20 regions, as depicted in FIG. 1: preauricular; submaxillary (denoted as 2 in FIG. 1); submental (shown at 1 in FIG. 1); upper, middle, and lower jugular (depicted at 3, 4 and 5 respectively); upper, middle, and lower posterior cervical (depicted at 6, 7 and 8); and supraclavicular (depicted at 9); both ipsilateral and contralateral to the primary lesion. Separate distributions were compiled for each of ten different primaries, as illustrated in FIG. 2: oral tongue (depicted at "O"), floor of mouth ("F"), retromolar trigone ("R"), soft palate ("S"), tonsillar fossa ("T"), base of tongue ("B"), oropharyngeal walls, supraglottic larynx, hypopharynx, and nasopharynx. These are be termed the "old data".

Byers collected detailed histological data on 584 patients with previously untreated squamous cell carcinomas of the head and neck (in Head Neck Surgery, 10

(1988) at 160–167). The status of 22 nodal clusters (right and left submaxillary; submental; supraclavicular; suboccipital; paratracheal; upper, middle, and lower jugular; and upper, middle and lower posterior cervical) was reported. Twenty-two different types of primary lesions were analyzed ranging form the upper lip to the esophagus. These will be termed the "new data." Not all of these patients had clinically positive nodes. Thus the cancer was probably detected in an earlier stage than in the old data.

A subset of nodes and primaries from each study was selected for creating the MDS database used by the present invention. No more data were discarded than necessary to form corresponding input from each study, and decisions about exclusions were all made before the results from WMDS were examined. Preauricular, suboccipital and paratracheal nodes were only recorded in one of the studies, so the remaining 18 nodal clusters (9 on each side) were used in this analysis. No primaries of the nasopharynx were recorded in the new data so only the nine other primaries that are common to both studies were used in this analysis. Thus, the subset found in both sets of data—18 nodal clusters, seen in FIG. 1, and 9 primaries, seen in FIG. 2—was selected for analysis. Each subset was first analyzed separately.

Proximities for each primary were calculated as differences in the number of positive clusters. Absolute values of 153 paired comparisons were calculated separately for each of the nine primaries (153=N*(N−1)/2 combinations of 18 clusters taken two at a time). For example, Lindberg reported 14 positive submaxillary clusters and 16 positive low-jugular clusters from primaries in the tonsil. The relatively small difference of 2 shows these two clusters collect approximately the same number of spreading tumor cells and should thus be "close together" in this abstract space, even though they are not anatomically adjacent. In contrast, 103 positive upper jugular clusters were reported. The "distance" from the upper jugular to the submaxillary clusters was thus calculated to be 89 ( 103−14 ). This relatively large difference shows that tumors more frequently metastasize to one of these clusters than the other, and thus these clusters can be considered to be more "distant" even though they are physically adjacent.

These proximity measures, positive differences between all possible pairs of nodal clusters, were collected into off-diagonal half matrices separately for each primary and submitted to SINDSCAL (Symmetric Individual Differences Scaling—see generally Pruzansky, How to use Sindscal, a computer program for individual differences in multidimensional scaling, Bell Laboratories, Murray Hill, N.J. 1983). The analysis was done separately at first for the old and new data. Each analysis was run several times with different starting configurations to assure that the reported solution was not a local minimum.

Random simulations determined the goodness of fit expected by chance. Exactly the same procedures that were applied to the data were repeated over 50 times with random numbers replacing the patients' data.

MDS solutions were created in spaces of several different dimensions. Variance accounted for always increased with the number of dimensions as seen in Table 1, up to a perfect fit in one less than the number of independent points:

TABLE 1

| | Variance Accounted for by Weighted Multidimensional Scaling in Various Numbers of Dimensions | | | | | |
|---|---|---|---|---|---|---|
| | Number of Dimensions | | | | | |
| | 1 | 2 | 3 | 4 | 5 ... | 10 |
| Old | 80.4 | 93.1 | 97.4 | 99.1 | 99.1 | 99.98 |
| New | 83.7 | 91.3 | 94.9 | 97.2 | 98.7 | 99.96 |
| Gain | | 10.1 | 4.0 | 2.0 | .8 | |

NOTE: Old and new data are from Lindberg and Byers as explained above. Gain is the average percentage improvement in VAF as the number of dimensions is increased by one.

General guidelines for how many dimensions should be included in the solution are the last large increase in VAF as the number of dimensions are increased by 1 and some interpretability in the solution. It is clear from Table 1, by gain in VAF, and FIG. 2, by the similarity of primaries' weights and midline projections, that a two-dimensional analysis is appropriate for both the old and the new data.

The two-dimensional MDS analysis explains significantly more of the data than expected by chance, with correlations above 0.95 in both the old and new data. The simulations show that such scaling is only expected to explain about 26% of the variance in random data and thus there is virtually no chance of obtaining such results by chance ($p << 10^{-30}$).

It will be recalled that an important result of an MDS analysis is a "map," that is, coordinates of points placed such that distances between points match the input proximities. In this analysis, points represent clusters of lymph nodes so the map is termed a nodalgram. These maps can be stretched differently for each source of input. In the data transformations underlying the present invention, weights of each dimension in the nodalgram are calculated for each primary.

The nodalgrams are not easily related to anatomical coordinates. It appears that neither the nodalgram from the old nor the new data can be derived from a linear transformation of normal anatomy. Although difficult to interpret at this time, these abstract maps still explain the data extremely well, however, as indicated above. This suggests that MDS taps a consistent underlying relationship within these data. Interestingly, the scaling of these two independent sets of data gives very similar results.

Because the results from these two sets of data were so similar, the data used in one embodiment of the illustrative method includes a combination of the two data sets in order to present one visualization that describes the pattern in all of the available data. Therefore, for actual use in making predictions, a new set of dissimilarity measures was derived by combining the probabilities of positive nodes in both data sets, and the results of WMDS of these combined data were used for visualization.

Since sample sizes are different in the two data sets, the raw data were first converted to percentages, and then these percentages were averaged to produce the expected probability of obtaining a positive node. There are 18 of these probabilities for each of the nine primaries. Dissimilarity measures were then calculated as the absolute value of all possible pairs of differences between different nodal clusters.

For example, the dissimilarity between nodal clusters 2 and 3 for primaries in the floor of the mouth (2nd primary or code=F) is (50/127+30/99)/2−(43/127+20.99)/2 =0.078, where the numerators (50, 43, 30 and 20) are found in the table shown in FIG. 7, and the denominators (127 and 99) are total cases of floor of mouth tumors in the old and new data sets respectively.

NOTE: in FIG. 7, "old" data are from Lindberg and "new" data are from Byers as explained above. Ipsilateral clusters are shown in FIG. 1 as black numbers on white circles; contralateral clusters are shown as white numbers on black circles. The Nodalgram is the "group stimulus space" from a SINDSCAL analysis of the data combined to indicated in the test with DIM=2, IRDATA=2, ITMAX=99 (but only 15 iterations were required), NMAT=9, NSTIM=18, IRN=7292 (but neither the solution nor VAF changed meaningfully with different starting configurations).

Figure 3:
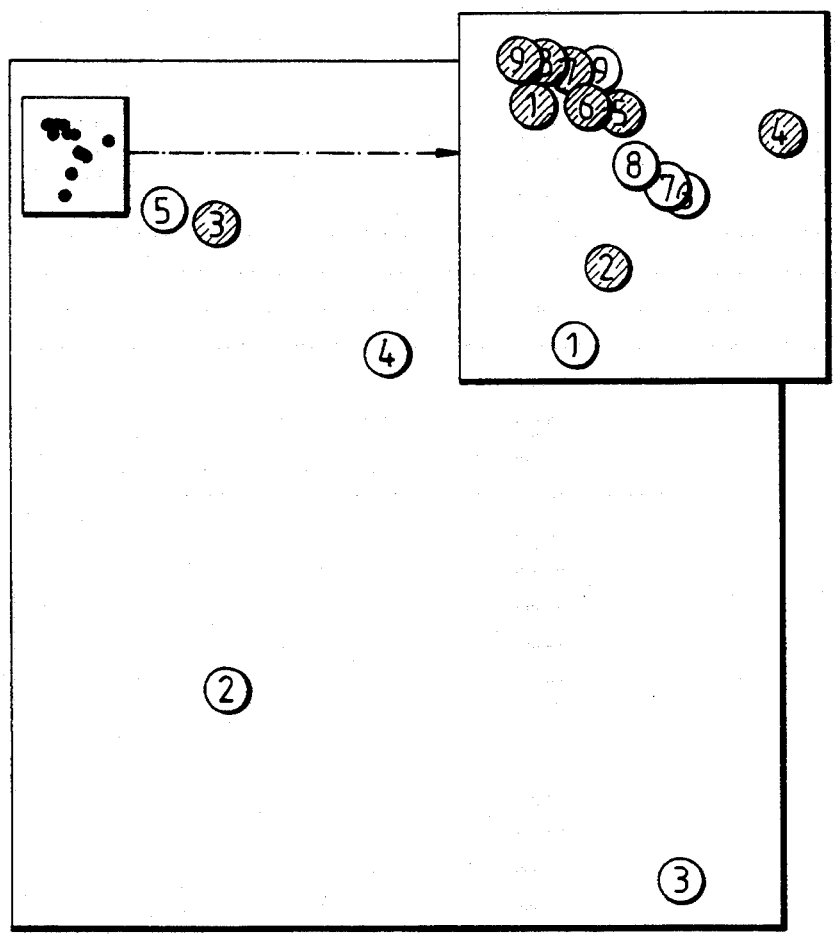
FIG. 3 is a graph illustrating the position of the lymph node clusters of FIG. 1 in nodalgram space.

Again, SINDSCAL produces a solution that explains over 94% of the variability in the combined data, considerably more than is expected by chance. FIGS. 7 and 3 show the coordinates of points, placed in a two-dimensional space, such that distances between these points correlate as closely as possible with the averaged dissimilarities. The positions of these points have, as in the previous analysis, no discernable relationship to the anatomical positions of the lymph nodes.

Figure 4:
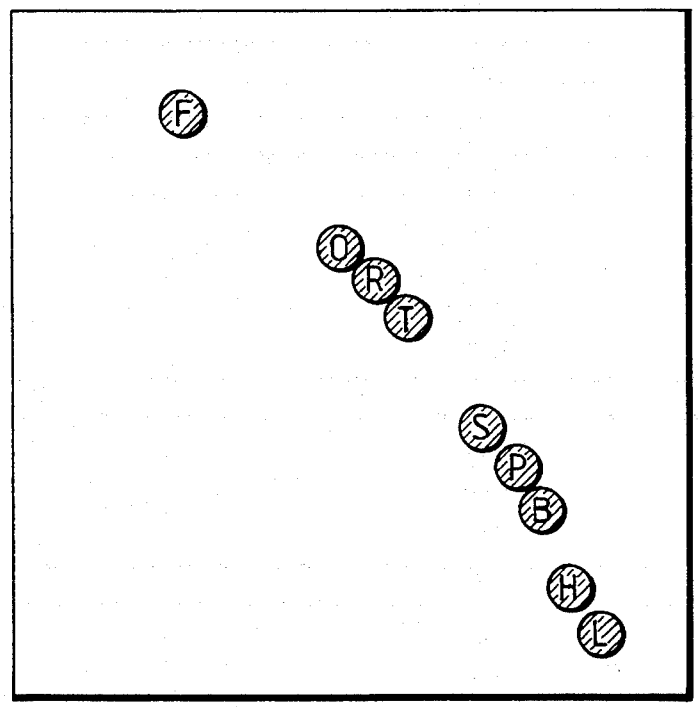
FIG. 4 is a graph illustrating the position of the weights assigned to the primary tumor sites of FIG. 2.

Interpretability in these data is best seen in the primary weights of FIG. 4. This depicts the extent to which metastases from each different primary spread along the dimensions of the nodalgram (whatever they are). For example, note that the floor of mouth has a larger vertical than horizontal coordinate in the old primary weights (point F in FIG. 4). This means that metastases from this primary spread more along the vertical than horizontal dimensions of the nodalgram. Lesions of the larynx, in contrast, spread along the horizontal axis (point L in FIG. 4), and lesions of the retromolar trigone spread evenly along both imaginary dimensions (point-R). FIG. 2 shows the midline projections of these primaries. Note that the primary weights resemble the primaries' normal anatomical positions.

FIG. 8 shows the primary weights derived from the weighted multidimensional scaling. The next to the last column in FIG. 8 shows the correlations between computed scores and scalar products for each primary provided by the WMDS. NOTE: 0.5084 and 0.4208 added to primary weights to adjust X and Y primary weights respectively.

The mathematical analysis of WMDS, which was designed to deal with the subjective perceptions of different human subjects to a set of different stimuli, thus has been successfully used to explain the spread of head and neck cancers. But usually the stimuli are colors or types of food, and the individuals are different observers; that is, stimuli and subjects are traditionally very different entities. Recall, however, that in the present analysis "stimuli" are clusters of lymph nodes and "individuals" are primaries, so both spaces can be thought of as imaginary representations of human neck anatomy. Thus, a new method must be derived to relate the two traditionally separate configurations that are derived from WMDS.

In order to solve this problem of relating the coordinates of the nodalgram and the primary weights, the primary weights can be though of as determining the shape of an ellipse. It is then possible to solve for the center of the ellipse in the space of the nodalgram, so that distances to all of the points are maximally correlated with the raw data.

To do this, the primary weights first need minor adjustments so they will determine workable ellipses. Then the best center for this ellipse is found by repetitive search over the space of the nodalgram. Some of the primary weights need to be adjusted because they are negative. Primary weights should, in theory, be greater than zero, but because noise in WMDS is largely absorbed in these weights they can occasionally be slightly negative and should be interpreted as equal to zero (Schiffman et al., 1981 p. 167). Only three of the 18 weights are slightly negative, and this only occurs when the weight in the other dimension is very large as seen in FIG. 8. The amount of the most negative weight is added to each weight for each dimension, to make all the weights non-negative. Since the expansion of an infinitely skinny ellipse would never surround many points, each weight is increased further by an arbitrary amount equal to one-tenth of the maximum weight. Specifically, for each dimension the weights of each primary are adjusted according to the following formula:

$$W^*_{p,d} = W_{p,d} - \min(W_{.d}) + \max(W_{.d})/10. \quad (1)$$

where $W^*$ is an adjusted weight that replaces the weights ($W_{p,d}$) computed by SINDSCAL in all of the subsequent calculations; $p$ denotes the type of primary; $d$ denotes the dimension; and $\min(W_{.d})$ and $\max(W_{.d})$ define the range of weights over primaries for each dimension.

To find the best center for the expanding ellipse, an iterative process was used to calculate correlations between distances to all the points in the nodalgram and the raw data. Points were selected in even spacing of 0.01 units from −1.00 to +1.00; thus a total of 40401 points were evaluated for each primary. Specifically, distance was calculated for each primary and node according to the following formula;

$$D_{n,p} = \sqrt{\sum_d [(N_{n,d} - C_{p,d}) * \sqrt{(W^*_{p,d})}\,]^2} \quad (2)$$

where $N_{n,d}$ and $W^*_{p,d}$ are the points and adjusted weights from SINDSCAL. These 18 distances, $D_{n,d}$, were parametrically correlated with the raw data (using Pearson's r), and coordinates of a center ($C_{p,d}$) were found that maximized that correlation. These correlations are high as seen in FIG. 8, varying from a low of 0.979 to a high of 0.997. Thus in every instance these adjusted weights and expanding ellipses explained at least 95% of the data on nodal metastases.

Figure 5:
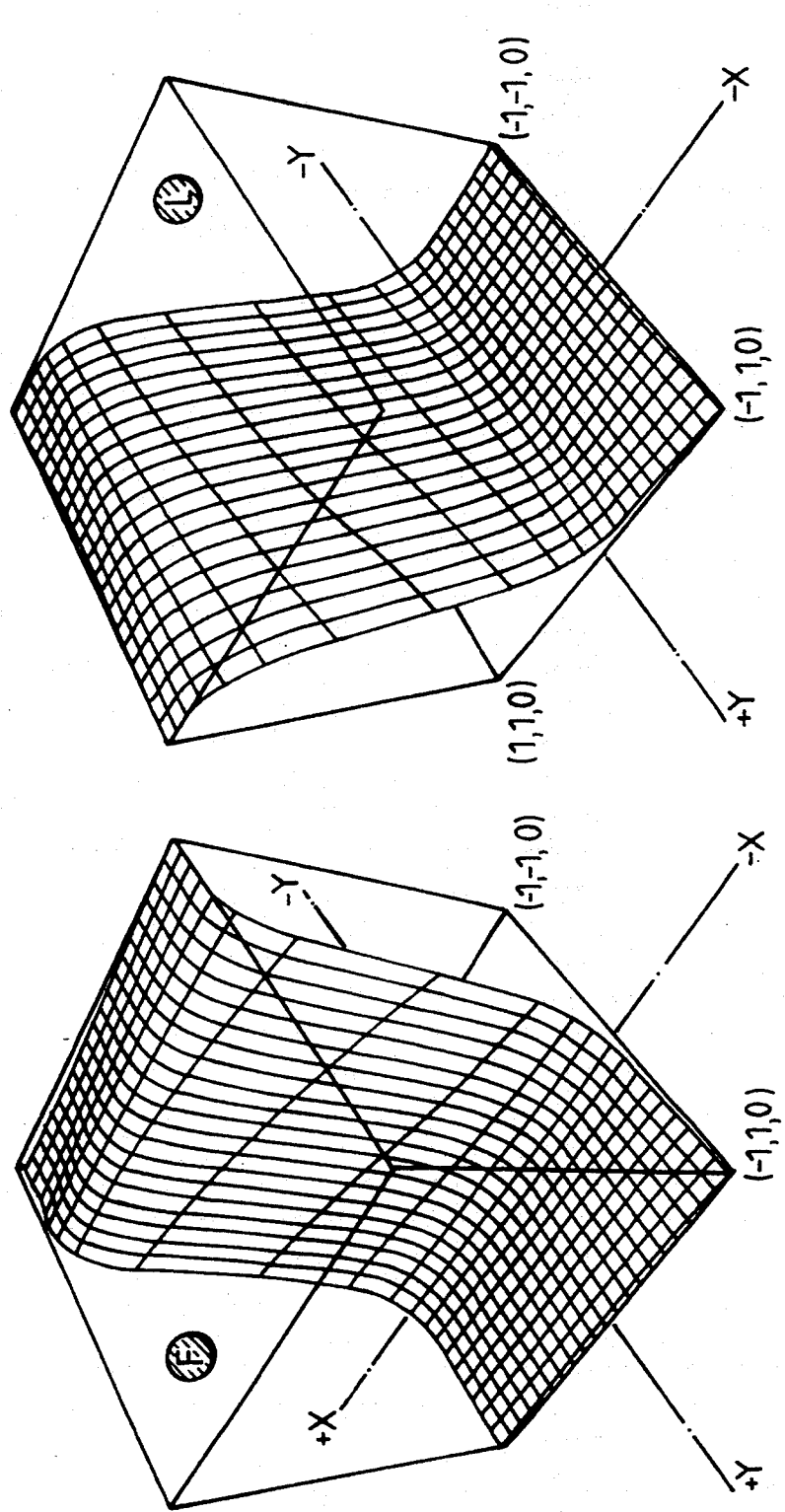
FIG. 5 is a wireframe graph illustrating the method of selecting the best location of a primary tumor site in nodalgram space.

Results from such a search for the center of two different primaries are shown in FIG. 5. Here, the correlation coefficient is shown on the Z axis (or as "height of the mountain"). The X and Y axes (analogous to north-south and east-west if this were a relief map) are the coordinates of the center of the ellipse, which were allowed to range between plus and minus 1. Note the smooth nature of this function, devoid of readily-discernible local maxima and minima.

The function rises from a flat valley in one corner of nodalgram space to a high plateau in the opposite corner. The exact position of the best center is thus somewhat arbitrary, as high correlations are found anywhere within the high plateau. It appears that the primaries may be thought of as regions (delimited by the topography of the high plateau) rather than as single points in the space of the nodalgram.

This representation of primaries as areas, not points, in the nodalgram makes some biological sense, because while the nodal clusters occupy a relatively small space within the normal neck, the different primaries can occupy a larger range. For example, the hypopharynx can extend as far superiorly as the epiglottis and as far inferiorly as the level of the second vertebra. It is thus reasonable that primaries might occupy a larger are of nodalgram space than individual nodal clusters.

Figure 6:
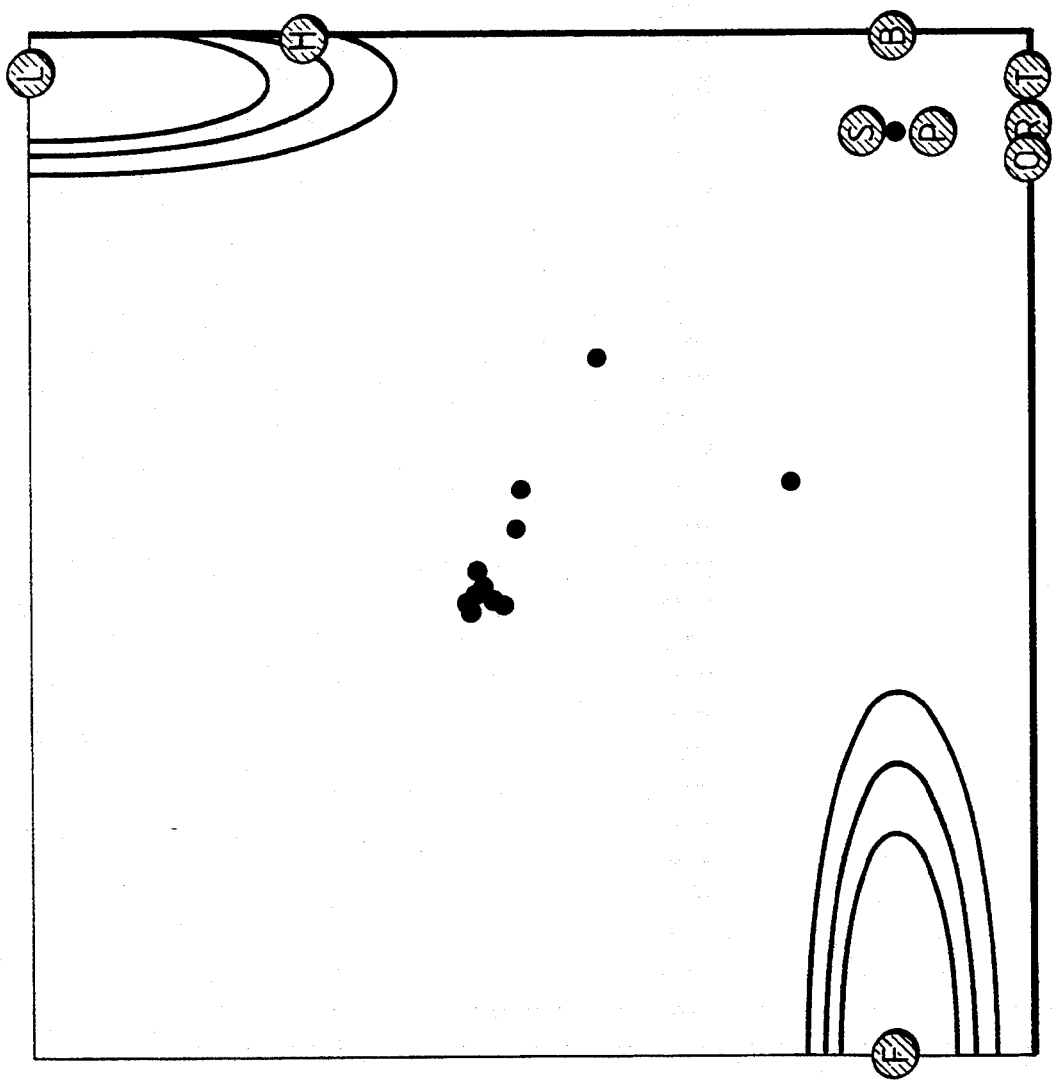
FIG. 6 is a graph indicating the locations of the lymph node clusters identified in FIG. 1 showing the superimposed primary site weights in nodalgram space as well as a set of sample ellipses originating from various primary sites.

The consistent structure within these data is again demonstrated by the plot of the best centers, as seen in FIGS. 8 and 6. These coordinates are related to the anatomical positions of the primaries (this relationship approaches statistical significance as evaluated by canonical correlation between the ellipses' best centers, FIG. 6, and the midsagittal projection of the primaries' normal anatomical locations, FIG. 2; Hoteling's $F_{4,8}=3.3$, $p=0.07$; but Pillai's and Wilk's tests are both significant at the 0.016 and 0.034 levels respectively). Additionally, a plot of the primary weights is closely correlated with the best centers ($F_{4,8}=3.76 p<0.0001$). These correlations between the positions of the primaries in real and imaginary space mean that the axes of the nodalgram can be related to anatomical dimensions. The X axis is related to anterior to posterior dimension and Y axis is related to the superior to inferior dimension, but only when these axes are referred to the primaries and not when they refer to nodal clusters.

The expanding ellipses, as shown in FIG. 6, can be used to predict metastases and these predictions can be visualized as described below. Thus while it may not be known why this analysis works, it demonstrably does work.

In a computer-generated visualization of one embodiment of the present invention, predicted metastases are represented by changing intensities, $I_{p,n,s}$, calculated for each primary for all the nodes and in each of several steps. These intensities vary from a minimum of 0 in all nodes in step 0, to a maximum of 1.0 in the closest node in the final step. These steps occur in the visualization as the head is rotated 1 degree. For a given primary and one of the many steps, the intensity at each node is calculated as $$I_{p,n.s}=[S/359 *D_{max}-(D_{n,p}-D_{min})]/D_{max} \quad (3)$$

where S runs from 0 to 359, and $D_{min}$ and $D_{max}$ are distances from the center to the nearest and farthest node respectively, with the provision that no intensity is less than zero.

This process can be thought of as expanding an ellipse, starting from some point ($C_{p,d}$) in nodalgram space and expanding until all of the nodes in this space are contained within the ellipse. The shape of the ellipse is determined by the primary weights (see equations 1 & 2). Thus if metastases from a particular primary (like from L in the upper right of FIG. 6) spread primarily along the x-axis of the nodalgram, the distances can be thought of as expansions of a relatively skinny ellipse. Note that because the ellipses are drawn as isodistance contours, their long axis is proportional to the lower weight and vice versa.

As the edge of the ellipse expands it encounters more and more nodes. The inside difference in equation 3 ($D_{n,p}-D_{min}$) assures that the ellipse encounters the nearest node on the first step. This was done because little is learned by visualizing the initial condition when no nodes are positive, although this "time" may be important in predicting when metastasis will start. Thus, on the first step the intensity of only the nearest node becomes slightly positive ($I_{p,nearest,1}>0$) and all the other intensities are negative and set to zero ($I_{p,<>near,1}=0$). The intensity of the nearest node then increases in linear steps until it reaches a maximum near 1.0 on the final step. Intensities of the other nodes are zero until the expanding ellipse reaches their coordinates in the nodalgram, that is until the step where $S/360*D_{max}>(D_{n,p}-D_{min})/D_{max}$. The intensities of these nodes then increase in the same linear steps. On the final step intensities are inversely proportional to distances from the center: the intensity of the nearest node is 1.0; the intensity of the most distant node has just turned positive; and intensities of all the other nodes are intermediate with intensities of the nodes close to the center of the ellipse in nodalgram space higher than intensities of more distant nodes. Correlations between these final intensities ($I_{p,n,359}$) and the raw data are seen as the Final Correlations in FIG. 8, varying from a low of 0.979 to a high of 0.997.

The visual demonstration of pathological processes provided by the present invention is expected to be of value in medical education. Video tapes of this visualization have been viewed by experienced head and neck surgeons, who state that the pattern is consistent with their experience. It is possible that surgeons in training, or physicians who lack the accumulated experience to form good subjective impressions about these patterns of spread might benefit from such visualizations. Such demonstrations might also help educate patients about the risks of exposure to the carcinogens that start this process.

The visual demonstration of the spreading process in one embodiment of the present invention may also be used in the clinical practice of a technique in accordance with the present invention, which relies on the use of the above-described WMDS results implemented by a computer. In clinical practice, a treating physician examining a patient having an identifiable primary tumor and one or more enlarged lymph nodes predicts the probable locations of other positive lymph nodes. First, the physician identified the location of the primary tumor, usually by visual inspection of the mucous membranes of the throat or other areas, or possibly by the use of high-resolution imaging such as computerized tomography or magnetic resonance imaging. The location of the most severely infected lymph nodes is then determined by lightly squeezing the neck between the fingers during an office visit. Having gathered this data, the treating physician enters the data into a computer having software containing the nodalgrams and the predictive algorithms described above. By the technique of expanding ellipses based on the precalculated weights or an equivalent technique, the computer generates a prediction of the probabilities that each cluster of nodes will be infected, perhaps displaying only the location and probability of infection associated with the clusters most at risk. Next, the treating physician can obtain high resolution images, by computerized tomography or an equivalent technique, of the nodes targeted by the computer as being at risk. After doing so, he scores the size of the node, the number of enlarged nodes in each cluster, the presence of any noticeable abnormality within the node, and any possible evidence of spread outside of lymphatic channels. Armed with this information, the physician enters the new data into the computer, which refines predictions based on this information. The imaging step is then repeated as necessary. This embodiment of the process is therefore an iterative one which converges when the last-examined nodal clusters appear to be free of disease.

Alternately, the physician might simply consult with the patient after running the initial analysis and decide which nodes need to be excised based on the initial prediction (from clinical observations of abnormally-enlarged nodes) of which nodes are most at risk. In consulting with the patient, the physician could also, of course, rely on the more refined data generated by the iterative procedure. The physician then passes this information on to the surgeon for use during the neck dissection.

This technique of the present invention may also be used during the surgery itself. Such use involves the presence of the computerized analysis system containing the nodalgrams in close proximity to the operating room. As individual clusters of nodes are excised, the pathologist scores the number of positive nodes in each cluster and provides an ordinal subjective impression of the extent of atypical cells. This data may be obtained visually or by examination of frozen sections obtained at the time of surgery. The incoming data are fitted to the general model, and the inclusion of each additional nodal cluster allows refinement of the predictions by slightly altering, for example, the effective values of the weights assigned to the primary or the center of the ellipse. The results are in the form of predictions of the next most likely node to be infected, which the surgeon then removes. Again, the process is iteratively continued until some previously agreed safety criterion, such as lack of infection, is reached in the last excised nodal cluster.

The present invention also improves the treatment of atypical cases by allowing the computer-generated predictions to be checked during surgery. Significant divergence between the predicted and actual results indicates an abnormal case. In such cases, the parameters of the model, such as the primary weights (which determine the ratio of the major to minor axis) and the center of the ellipse are recalculated by the previously-discussed center correlation optimization technique, and the model can continue to make useful predictions. Also, the surgeon is thus warned that more aggressive surgical intervention might be warranted. The method is also useful is the physician chooses to treat the cancer by chemotherapy or radiotherapy, since it can guide the radio- or chemotherapist in concentrating treatment in an analogous way to that in which it assists surgeons during neck dissections.

Postoperatively, the predictive method of the present invention may be used to reanalyze surgical results once permanently-mounted tissue sections are available. Relevant data include the percentage of mitotically-active cells in the tumor, subjective scores of the extent to which the tumor is differentiated, the extent of extra-capsular extension, the presence of keratin in the cancerous cells, the ratio of the size of the nucleus to the size of the tumor cells, the size of the nodes, the numbers of nodes in each cluster that are positive, and cell-biological markers of cultured tumor cells. Use may be made of those of the above factors which are susceptible to reduction to a single numerical index, which can be compared against the probability estimates derived from the computer model during surgery. This comparison provides a useful benchmark for the model's performance. Additionally, the gathering of several different indices of metastasis, which may be input into the model, allows the model to be systematically improved by the enlargement of the scope and amount of data therein. Furthermore, the computer predictions of the next most likely recurrence are saved as a guide to postoperative follow-ups. Patients who have a higher predicted risk should be scheduled for more frequent visits.

Lastly, the present method may also be useful in locating primary tumors when the treating physician has only found metastasized sites. In this embodiment, the treating physician gathers data on the location of the infected nodes, as described above, and inputs the data on infected nodes into the computer model. The model can spread the cancer backwards by the method of ellipses, finding the ellipse center and weights which best correlate with the observed result. This weight and center information can then be inverted to predict the location of the primary tumor causing the metastasis.

It might also be possible to determine if the spaces are different under conditions of distant metastases, multiple primaries, or recurrent tumors. Nodal clusters in other regions of the body could be added to this model and it is conceivable that eventually a full-body visualization could be prepared depicting both regional and distant metastases from a wide variety of tumors.

The above description of the embodiments is not intended to be exhaustive, and the proper scope of the present invention is limited only by the following claims.

The source code for expanding ellipses to visualize the spread of cervical metastases is provided as an appendix.

Appendix A: C routine to expand ellipses to visualize the spread of metastases, starting from array data generated by weighted multidimensional scaling.

```
#include <stdio.h>
#include <stdlib.h>
#include <math.h>
include <string.h>
#include <limits.h>
include <float.h> float       comp();
```

```c
/* e.c Version 3.0 Jan 1992 by Lincoln Gray
 * expand ellipses to visualize the spread of metastases
 * this program calculates ranks and distances of lymph nodes from a
 * "starting point" based on a multipdimensional scaling solution of cervical
 * metastases and writes a file of intensities
 */ main()
{
        /* these are the variables for writing the intensity file */
        int     line,                   /* each line of output */
                nlines=360 ,            /* how many lines to write */
                rnodes,                 /* how many stimuli in raw data matrices */
                maxline=359,            /* what line to end lighting */
                onoff=0,                /* 0 for graded lights, 1 for fully on when on */
                wait=0;                 /* 0 for lights starting on line 0, 1 for sort[0] */
        float   lightlevel,             /* the intensity of each node */
                linelevel,              /* criterion distance for this line */
                fll[18],                /* final light level */
                span,                   /* range of distances */
                lowspan,                /* least distance or 0, depending on wait*/
                shiftdist;              /* distance - lowspan */
        FILE    *fintf;
        char    outfile[20]="int";

/* declare the variables */
        int             i, j,           /* indices of loops */
                        ndims,          /* number of dimensions in the solution */
                        nprimaries,     /* how many matrices into SINDSCAL */
                        nnodes,         /* how many stimuli in each matrix */
                        maxassym = 10,  /* prevent infinitely skinny elipsoids*/
                        ptype,          /* index for the type of primary tumor */
                        rank[50];       /*nodes are encountered in which order */ char            filnam[8] = {"\0\0\0\0\0\0\0"},
                                        /* string to hold the file name */
                        label[80],
                        ordstr[9][3]={"st","nd","rd","th"};
        float           nodalgram[50][9],
                                        /* coordinates of the nodes in n-space */
                        primaryweight[12][9],
                                        /* weights for each primary and dimension */
                        center[9][9],   /* best starting point */
                        r,prob,z,B0,B1, /* for pearsn */
                        fudgeweight,
                        rawdata[18],    /* # pos nodes in raw data list */
                        normdata[18],   /* % or max pos nodes in raw data list */
                        xmax,           /* max of raw data */
                        dist[50],       /* calculated distance to each node */
                        sort[50];       /* dummy array to hold sorted distances */

/*
         * this section opens and reads the data files.
         */
        FILE            *fp,*fraw,*fcntr;
        /*printf("enter name of data file: ");*/
        gets(filnam);
        strcat(outfile,filnam);
        strcat(filnam, ".dat");
        fp = fopen(filnam, "r");
        fgets(label,80,fp);
        /*printf(label);*/
        fscanf(fp, "%d %d %d", &ndims, &nprimaries, &nnodes);
        /*printf("\n DIM = %d; NO. Primaries = %d, NO. nodes = %d",
                ndims,nprimaries,nnodes);*/
        for (i = 0; i < ndims; i++)
                for (j = 0; j < nprimaries; j++)
                        fscanf(fp, "%f", &primaryweight[j][i]);
        for (i = 0; i < ndims; i++)
                for (j = 0; j < nnodes; j++)
                        fscanf(fp, "%f", &nodalgram[j][i]);
        filnam[2]=0;
        strcat(filnam,".cntr");
        fcntr=fopen(filnam,"r");
```

```
        filnam[1]=0;
        strcat(filnam,".raw");
        fraw=fopen(filnam,"r");
        fscanf(fraw,"%d",&rnodes);
        if(rnodes!=nnodes)printf(" Error in #of nodes %d %d\n",nnodes,rnodes);
        /* this reads the best centers */
        for (ptype = 0; ptype < nprimaries; ptype++)
                fscanf(fcntr,"%f %f",&center[ptype][0],&center[ptype][1]);
        /*for (j = 0; j < nnodes; j++)
                {printf("\n node # %d is at point ",j);
                for (i = 0; i < ndims; i++)
                        printf(" %f ", nodalgram[j][i]);
                }
        for (j = 0; j < nprimaries; j++)
                {printf("\n Primary # %d has weights ",j);
                for (i = 0; i < ndims; i++)
                        printf(" %f ", primaryweight[j][i]);
                }
         this section adjusts primary weights to be > 0
        * and further that the minimum asymmetry is > some level
        */
        for (i = 0; i < ndims; i++)
                {for (j = 0; j < nprimaries; j++)
                        sort[j]=primaryweight[j][i];
                qsort(sort, nprimaries, sizeof(float), comp);
                fudgeweight=fabs((double)sort[0])+sort[nprimaries-1]/maxassym;
                for (j = 0; j < nprimaries; j++)
                        primaryweight[j][i]+=fudgeweight;
                }
        /*for (j = 0; j < nprimaries; j++)
                {printf("\n Primary # %d has ADJUSTED weights ",j);
                for (i = 0; i < ndims; i++)
                        printf(" %f ", primaryweight[j][i]);
                }
        printf("\n");
         * this final section asks for input from the operator to define the
         * type of the primary lesion and the starting point for the
         * expanding elipse
         */
        /*printf("enter the type of primary: ");
        scanf(" %d", &ptype);
        sprintf(label,"%02d",ptype);
        strcat(outfile,label);*/
        strcat(outfile,".dat");
        fintf=fopen(outfile,"w");
        /*printf(" Primary has ADJUSTED weights ",j);
        for (i = 0; i < ndims; i++)
                printf(" %f ", primaryweight[ptype][i]);
        printf("\n"); */
        /*printf("enter starting point as real coordinates: ");
        for (i = 0; i < ndims; i++)
                scanf("%f", &center[i]);*/
        /*
         * the formula for an elipse is ((x-x0)/a)**2 + ((y-y0)/b)**2 +
         * ((z-z0)/c)**2 = 1 a = a0 + n0a*t; b = b0 + n0b*t; c = c0 + n0c*t
         */
        /*
         * distances are calculated in a weighted multi-dimensional euclidean
         * space
         */
        for (ptype=0; ptype<nprimaries; ptype++) {
        for (j = 0; j < nnodes; j++) {
                dist[j] = 0;
                for (i = 0; i < ndims; i++)
                        {dist[j] += pow((double)
                                        ((nodalgram[j][i] - center[ptype][i]) *
                                        sqrt((double) primaryweight[ptype][i])),
                                        (double) 2);
/*printf(" %d %d %d %f %f %f %f\n",
j,i,ptype,nodalgram[j][i],center[i],primaryweight[ptype][i],dist[j]);*/
                        }
                dist[j] = sqrt((double) dist[j]);
        /*printf(" The distance to point %d is %f \n",j,dist[j]); */
                sort[j] = dist[j];
                /*printf (" %5.3f,",dist[j]);*/
```

```
        }
        /*printf (" \n");*/
/* finally the calculated distances are sorted and the order in which
 * the nodes would be encountered by an expanding elipse are
 * determined
 */
qsort(sort, nnodes, sizeof(float), comp);
for (j = 0; j < nnodes; j++)
        for (i = 0; i < nnodes; i++)
                if (dist[j] == sort[i])
                        rank[i] = j;
/*for (j = 0; j < nnodes; j++) {
        if (j < 3)
                i = j;
        else
                i = 3;
        printf(" %2d%s node encountered is # %d at distance %f\n",
                j + 1, ordstr[i], rank[j], sort[j]);
                        }*/
/* now the distances are written to a file for input to view.c */
lowspan=sort[0]*wait; /* 0 for start on line 0, min dist for wait*/
span=sort[nnodes-1]-lowspan;
for (line=0;line<nlines;line++)
        {linelevel= span * ((float)line/maxline);
        for(j=0;j<nnodes;j++)
                {shiftdist=dist[j];
                if (wait==0) shiftdist -= sort[0];
                if(linelevel<shiftdist)
                                lightlevel=0.;
                                else if (onoff==1)
                                        lightlevel=1.0;
                                else lightlevel=(linelevel-shiftdist)/span;
                        if (lightlevel>1.0)lightlevel=1.0;
                        fprintf(fintf,"%4.2f ",lightlevel);
                        if(line==(nlines-1))fll[j]=lightlevel;
                        }
                fprintf(fintf,"\n");
                }
                for (j = 0; j < nnodes; j++)
                  fscanf(fraw,"%f",&rawdata[j]);
                  fmax(nnodes,rawdata,&xmax);
                 for (j = 0; j < nnodes; j++)
                   normdata[j]=rawdata[j]/xmax;
        pearsn(normdata,fll,nnodes,&r,&B0,&B1,&prob,&z);
        printf(" %d %f \n",ptype,r);
                }
        fclose(fintf);
}
/* compare two floats, for qsort */
float
comp(const float *x, const float *y)
{
        return *x - *y;
}

/* pearsn.c calculates r,
from Press, W.H., Flannery, B.P., Teukolsky, S.A. and Vettering, W.T.
Numerical Recipes in C. 1988. Cambridge University Press.
*/
#define TINY 1.0e-20
void pearsn(x,y,n,r,B0,B1,prob,z)
float x[],y[],*r,*B0,*B1,*prob,*z;
int n;
{
int j;
float yt,xt,t,df;
float syy=0.0,sxy=0.0,sxx=0.0,ay=0.0,ax=0.0;
/*float betai(),erfcc();*/
for (j=0;j<n;j++){
ax += x[j];
ay += y[j];
}
ax /= n;
ay /= n;
for (j=0;j<n;j++){
```

```
xt=x[j]-ax;
yt=y[j]-ay;
sxx += xt*xt;
syy += yt*yt;
sxy += xt*yt;
}
*r=sxy/sqrt((double)sxx*syy);
*B1=sxy/sxx;
*B0=ay-sxy/sxx*ax;
*z=0.5*log((1.0+(*r)+TINY)/(1.0-(*r)+TINY));
df=n-2;
t=(*r)*sqrt(df/((1.0-(*r)+TINY)/(1.0+(*r)+TINY)));
/**prob=betai(0.5*df,0.5,df/(df*t*t));*/
}
void fmax(n,x,xmax)
int n;
float x[],*xmax;
{
int j;
*xmax=FLT_MIN;
for (j=0;j<n;j++)
if(x[j]>*xmax)*xmax=x[j];
}
```

Appendix B: C routine interpolating location of primary from data on infected nodes and array data from WMDS.

```
#include <stdio.h>
#include <stdlib.h>
#include <math.h>
include <string.h> float   comp();

/* findcenter.c Version 1.0 June 1991 by Lincoln Gray
 attempts to find the coordinates of a primary by looking for
 the best correlation between distances of expanding elipsoids
 for various "centers" and the number of positive nodes in the raw data
 */ main()
{
        /* declare the variables */ int             i, j,              /* indices of loops */
                        ndims,             /* number of dimensions in the solution */
                        nprimaries,        /* how many matrices into SINDSCAL */
                        nnodes,            /* how many stimuli in each matrix */
                        rnodes,            /* how many stimuli in raw data matrix */
                        maxassym = 10,     /* prevent infinitely skinny elipsoids*/
                        scale = 10,        /* grain to march through space */
                        ptype,             /* index for the type of primary tumor */
                        c1,c2,             /* indices for varying centers */
                        rank[18];          /* which nodes are encountered in which order */ char            filnam[8] = {"\0\0\0\0\0\0\0"},
                                           /* string to hold the file name */
                        label[80],
                        ordstr[4][3] = {"st","nd","rd","th"};
                                           /* make ordinal for output */
        float   nodalgram[18][4],
                primaryweight[12][4],      /* weights for each primary and dimension */
                        fudgeweight,
                        center[4],         /* where to start */
                        dist[18],          /* calculated distance to each node */
                        rawdata[18],       /* # pos nodes in raw data list */
                        xbest,ybest,       /* positions with best r */
                        rmax,              /* best r for a primary */
```

```
                xworst,yworst,  /* positions with worst r */
                rmin,           /* worst r for a primary */
                r,prob,z,       /* for call to pearsn */
                sort[18];       /* dummy array to hold sorted distances */
/*
 * this section opens and reads the data files.
 */
FILE        *fp, *fraw;
printf("enter name of data file: ");
gets(filnam);
strcat(filnam, ".dat");
fp = fopen(filnam, "r");
fgets(label,80,fp);
printf(label);
fscanf(fp, "%d %d %d", &ndims, &nprimaries, &nnodes);
printf("\n DIM = %d; NO. Primaries = %d, NO. nodes = %d",
        ndims,nprimaries,nnodes);
for (i = 0; i < ndims; i++)
        for (j = 0; j < nprimaries; j++)
                fscanf(fp, "%f", &primaryweight[j][i]);
printf("\n Primary Weights");
for (j = 0; j < nprimaries; j++)
        printf("\n Primary # %d %f %f",
                j, primaryweight[j][0], primaryweight[j][1]);
for (i = 0; i < ndims; i++)
        for (j = 0; j < nnodes; j++)
                fscanf(fp, "%f", &nodalgram[j][i]);
printf("\n Nodalgram dimensions");
for (j = 0; j < nnodes; j++)
        printf("\n node # %i %f %f",
                j, nodalgram[j][0], nodalgram[j][1]);
filnam[1]=0;
strcat(filnam,".raw");
fraw=fopen(filnam,"r");
fscanf(fraw,"%d",&rnodes);
if(rnodes!=nnodes)printf(" Error in #of nodes %d %d\n",nnodes,rnodes);
/* this section adjusts primary wieghts to be > 0
 * and further that the minimum asymmetry is > some level
 */
for (i = 0; i < ndims; i++)
        {for (j = 0; j < nprimaries; j++)
                sort[j]=primaryweight[j][i];
        qsort(sort, nprimaries, sizeof(float), comp);
        fudgeweight=fabs((double)sort[0])+sort[nprimaries-1]/maxassym;
        printf("\n Fudgeweight %i = %f",i,fudgeweight);
        for (j = 0; j < nprimaries; j++)
                primaryweight[j][i]+=fudgeweight;
        }
printf("\n Adjusted Primary Weights");
for (j = 0; j < nprimaries; j++)
        printf("\n Primary # %i %f %f",
                j, primaryweight[j][0], primaryweight[j][1]);
for (ptype = 0; ptype < nprimaries; ptype++)
        {
        for (j = 0; j < nnodes; j++)
        fscanf(fraw,"%f",&rawdata[j]);
        rmax=0;
        rmin=-1;
        for (c1=-100;c1<100;c1++)
        for (c2=-100;c2<100;c2++)
        {center[0]=c1/100.;
        center[1]=c2/100.;
for (j = 0; j < nnodes; j++) {
        dist[j] = 0;
        for (i = 0; i < ndims; i++)
                dist[j] += pow((double)
                        ((nodalgram[j][i] - center[i]) *
                        sqrt((double) primaryweight[ptype][i])),
                        (double) 2);
        dist[j] = sqrt((double) dist[j]);
}
pearsn(rawdata,dist,nnodes,&r,&prob,&z);
if(r<rmax){xbest=center[0];ybest=center[1];rmax=r;}
```

```
            if(r>rmin){xworst=center[0];yworst=center[1];rmin=r;}
        }
        printf("\n Primary # %d has best correlation %f at %f %f \n "
                        ,ptype,rmax,xbest,ybest);
        printf("\n            worst correlation %f at %f %f \n "
                        ,rmin,xworst,yworst);
    }
}
/* compare two floats, for qsort */
float
comp(const float *x, const float *y)
{
        return *x - *y;
}

/* pearsn.c calculates r,
from Press, W.H., Flannery, B.P., Teukolsky, S.A. and Vettering, W.T.
Numerical Recipes in C. 1988. Cambridge University Press.
*/
#define TINY 1.0e-20
void pearsn(x,y,n,r,prob,z)
float x[],y[],*r,*prob,*z;
int n;
{
int j;
float yt,xt,t,df;
float syy=0.0,sxy=0.0,sxx=0.0,ay=0.0,ax=0.0;
/*float betai(),erfcc();*/
for (j=0;j<n;j++){
ax += x[j];
ay += y[j];
}
ax /= n;
ay /= n;
for (j=0;j<n;j++){
xt=x[j]-ax;
yt=y[j]-ay;
sxx += xt*xt;
syy += yt*yt;
sxy += xt*yt;
}
*r=sxy/sqrt((double)sxx*syy);
*z=0.5*log((1.0+(*r)+TINY)/(1.0-(*r)+TINY));
df=n-2;
t=(*r)*sqrt(df/((1.0-(*r)+TINY)/(1.0+(*r)+TINY)));
/**prob=betai(0.5*df,0.5,df/(df*t*t));*/
}
```

What is claimed is:

1. A computer-executed method of analyzing a signal encoding machine-generated patient image data to identify zero or more lymph nodes having an elevated risk of containing cancer cells in a patient having a primary tumor, said method comprising:

(a) receiving a first signal encoding the location of said primary tumor;

(b) generating a second signal encoding the location of zero or more lymph nodes in said patient which appear to be abnormal or enlarged;

(c) generating, as a function of said first signal and said second signal, a third signal encoding (i) an index of metastasis likelihood for a cluster of lymph nodes for said patient and (ii) a location for said cluster of lymph nodes for said patient; and (d) displaying a representative of said third signal;

(e) wherein the location of said zero or more lymph nodes in said patient which appear to be abnormal or enlarged, encoded in said second signal, is derived from a signal encoding computerized tomography image data of said patient.

* * * * *